United States Patent
Farrell et al.

(10) Patent No.: US 10,973,944 B1
(45) Date of Patent: Apr. 13, 2021

(54) FRAGRANCE DISPENSER WITH FRAGRANCE CONSERVATION FEATURES

(71) Applicant: Rimports, LLC, Provo, UT (US)

(72) Inventors: Alan K. Farrell, Salt Lake City, UT (US); Joe Robinson, Lehi, UT (US)

(73) Assignee: Rimports, LLC, Provo, UT (US)

( * ) Notice: Subject to any disclaimer, the term of this patent is extended or adjusted under 35 U.S.C. 154(b) by 82 days.

(21) Appl. No.: 16/358,640

(22) Filed: Mar. 19, 2019

Related U.S. Application Data

(63) Continuation-in-part of application No. 29/600,629, filed on Apr. 13, 2017, now Pat. No. Des. 843,556, and a continuation-in-part of application No. 29/592,630, filed on Jan. 31, 2017, now Pat. No. Des. 849,540.

(51) Int. Cl.
| | |
|---|---|
| *A61L 9/14* | (2006.01) |
| *F24F 6/08* | (2006.01) |
| *A61L 9/12* | (2006.01) |

(52) U.S. Cl.
CPC .............. *A61L 9/14* (2013.01); *A61L 9/122* (2013.01); *A61L 9/127* (2013.01); *F24F 6/08* (2013.01); *A61L 2209/13* (2013.01)

(58) Field of Classification Search
CPC .... F24F 6/08; A61L 9/14; A61L 9/122; A61L 9/127
See application file for complete search history.

(56) References Cited

U.S. PATENT DOCUMENTS

| | | |
|---|---|---|
| 3,254,844 A | 3/1964 | Blasnik et al. |
| D198,054 S | 4/1964 | Lowry |
| D213,213 S | 1/1969 | Horton et al. |
| D254,930 S | 5/1980 | Mandon et al. |
| D355,601 S | 2/1995 | Buettner et al. |
| D357,628 S | 4/1995 | Vasas |
| D399,658 S | 10/1998 | Nosella |
| D400,442 S | 11/1998 | Nosella |
| D404,459 S | 1/1999 | Furner et al. |
| 6,061,950 A | 5/2000 | Carey et al. |
| D465,019 S | 10/2002 | Wu |
| D484,414 S | 12/2003 | Kerr |
| 6,862,403 B2 * | 3/2005 | Pedrotti .............. A01M 1/2072 392/392 |
| D506,136 S | 6/2005 | Wilde et al. |
| D538,177 S | 3/2007 | Dretzka |

(Continued)

*Primary Examiner* — Robert A Hopkins
(74) *Attorney, Agent, or Firm* — Dentons Durham Jones Pinegar

(57) ABSTRACT

Fragrance dispensers with features that are capable of reducing wastage of fragrance, or of conserving fragrance, are disclosed. Such a fragrance dispenser may have a configuration that collects fragrance that is expelled from the fragrance dispenser, but has not vaporized or atomized sufficiently to dissipate into the environment, as well as fragrance that condenses immediately after it has been expelled from the fragrance dispenser. A spill-resistant bottle that may be used with a fragrance dispenser has a shape that orients an opening of the bottle in a somewhat upward orientation to prevent fragrance from spilling out when the bottle is tipped over. Fragrance dispensers with configurations that generate vortices to deliver fragrance into the surrounding environment are also disclosed.

21 Claims, 5 Drawing Sheets

(56) References Cited

U.S. PATENT DOCUMENTS

| | | |
|---|---|---|
| D543,846 S | 6/2007 | Kitamura et al. |
| D556,312 S | 11/2007 | Majerowski et al. |
| D581,287 S | 11/2008 | Tran et al. |
| D611,344 S | 3/2010 | Longacre |
| D631,355 S | 1/2011 | Barsoumian |
| D646,973 S | 10/2011 | Flanagan-Kent et al. |
| D673,253 S | 12/2012 | Mack |
| 9,144,621 B1 | 9/2015 | Finlay |
| 9,573,154 B2 * | 2/2017 | Bretillot ................ B05B 12/081 |
| D797,883 S | 9/2017 | Dalmau Arnal et al. |
| D802,422 S | 11/2017 | Laib et al. |
| D816,203 S | 4/2018 | Valentino et al. |
| D834,693 S | 11/2018 | Robinson et al. |
| D835,771 S | 12/2018 | Farrell et al. |
| D843,556 S | 3/2019 | Robinson et al. |
| D849,540 S | 5/2019 | Robinson et al. |
| D861,846 S | 10/2019 | Goodsell |

\* cited by examiner

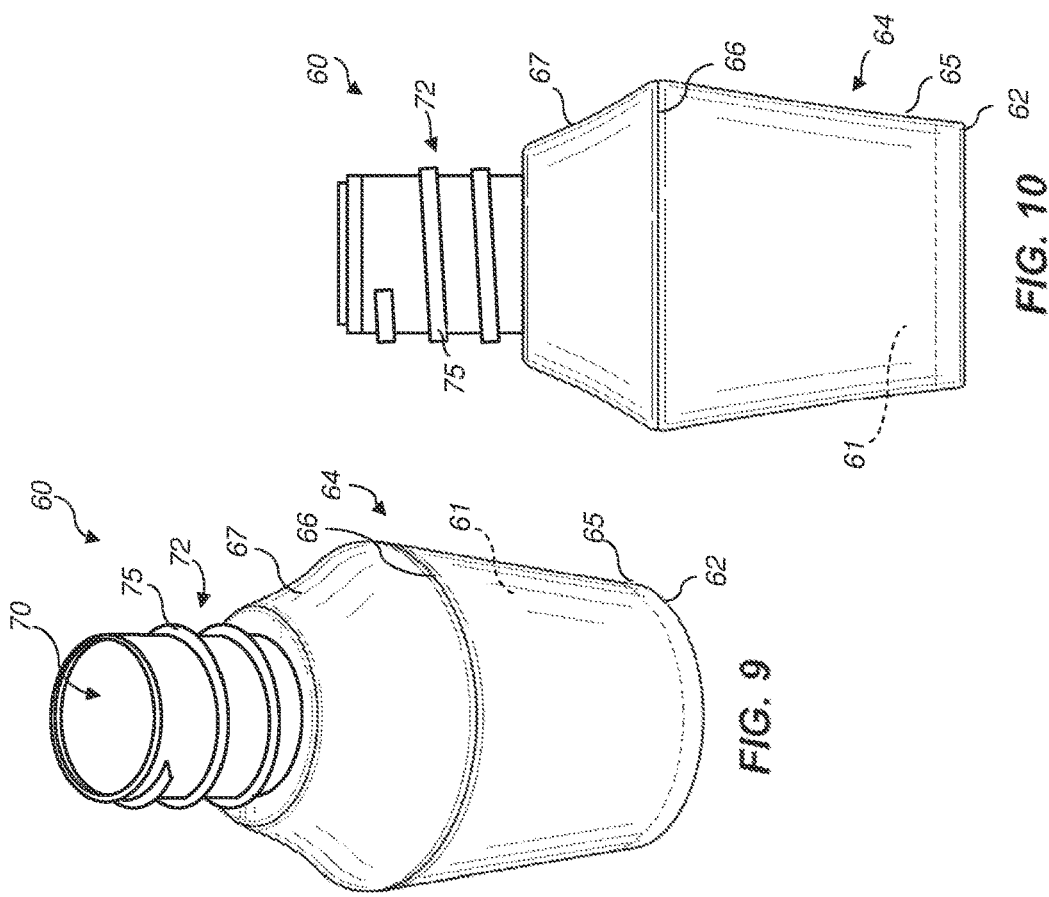
FIG. 10
FIG. 9
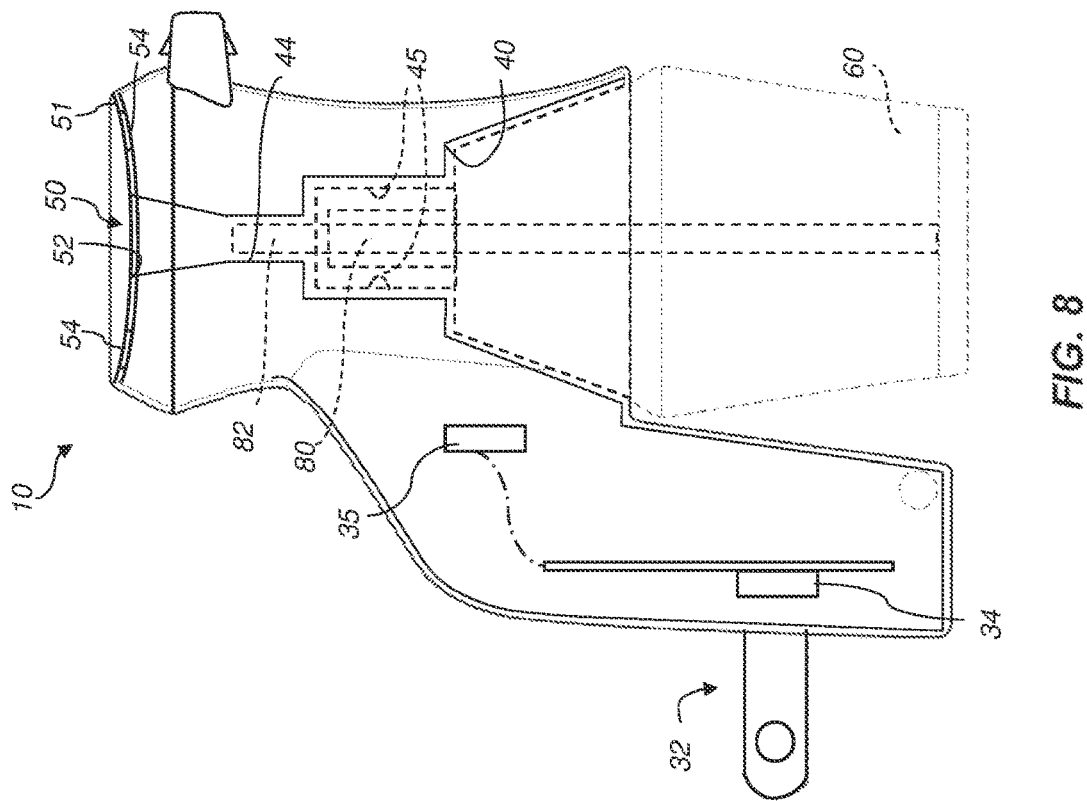
FIG. 8

FRAGRANCE DISPENSER WITH FRAGRANCE CONSERVATION FEATURES

CROSS-REFERENCE TO RELATED APPLICATIONS

This application is a continuation-in-part of U.S. Design patent application No. 29/600,629, filed on Apr. 13, 2017 and titled CONCAVE VENT FOR A FRAGRANCE DISPENSER ("the '629 Design application"), now U.S. Pat. D843,556, issued Mar. 19, 2019. This application is also a continuation-in-part of U.S. Design patent application No. 29/592,630, filed on Jan. 31, 2017 and titled BOTTLE FOR A FRAGRANCE DISPENSER ("the '630 Design application"), U.S. Patent D849,540, issued May 28, 2019. The entire disclosures of the '627 Design application and the '630 Design application are hereby incorporated herein.

TECHNICAL FIELD

This disclosure relates generally to fragrance dispensers and, in some embodiments, to electrically operated fragrance dispensers that are configured to be coupled to electrical outlets. Even more specifically, this disclosure relates to fragrance dispensers with features that are capable of reducing wastage of fragrance, or of conserving fragrance.

SUMMARY

In one aspect, a fragrance dispenser according to this disclosure has a configuration that collects fragrance that has been emitted thereby without being sufficiently vaporized or atomized to be dispersed into the environment in which the fragrance dispenser is located. In various embodiments, such a fragrance dispenser may include a fragrance emission vent with a configuration that enables it to collect any fragrance that has been dispensed, but quickly condenses or precipitates, and then returns such fragrance to a reservoir, from which the fragrance may be subsequently dispersed. Such a fragrance emission vent may be concave in shape and direct any fragrance collected thereby into an opening of a reservoir that holds the fragrance.

A configuration of the fragrance emission vent may also generate an airflow that enhances dispersal of fragrance into an environment into which the fragrance dispenser is located. As a nonlimiting example, a configuration of the fragrance emission vent may generate a vortex or a plurality of vortices as air flow therethrough and/or is as air is emitted thereby. The generation of a vortex or a plurality of vortices may optimize or otherwise tailor the direction and/or distance that fragrance may be thrown from the fragrance emission vent and, thus, from the fragrance dispenser.

In another aspect, a fragrance dispenser according to this disclosure may include a reservoir, such as a bottle, that has a shape that prevents the fragrance contained thereby from spilling out, even when the reservoir is knocked over. Such a reservoir may be referred to as a "spill-resistant reservoir." A shape of the reservoir may prevent its opening from being oriented toward or even parallel to a horizontal surface (e.g., a floor, a countertop, a tabletop, etc.) that supports the reservoir, even when the reservoir rests on its side; the shape of the reservoir may cause it to rest on a surface in such a way that its opening is always directed away from the surface. Such a reservoir may include a base, a sidewall with a lower portion oriented at an obtuse angle to the base and an upper portion oriented at an obtuse angle to the lower portion of the sidewall, and an opening at or adjacent to an uppermost extent of the upper portion of the sidewall. Optionally, the opening may be defined by a neck that extends from the uppermost extent of the upper portion of the sidewall. Relative lengths and orientations of the lower portion of the sidewall, the upper portion of the sidewall, the optional neck, and a wick, if any, that protrudes from the opening may cause the reservoir to rest in an orientation that causes the reservoir to rest on the lower portion of its sidewall, which positions the opening of the reservoir away from the surface at an angle that prevents the contents of the reservoir from spilling out of the opening.

Methods for dispensing fragrance into an environment are also disclosed. Such a method may include preserving fragrance by collecting fragrance that has not atomized or vaporized sufficiently to be dispersed, or fragrance that has condensed shortly after being emitted, and returning the fragrance that has been collected to a reservoir that contains a volume of the fragrance. A method for dispensing fragrance may include preserving fragrance by using a reservoir with a shape that prevents spillage when the reservoir is knocked over onto a horizontal surface (e.g., a floor, a countertop, a tabletop, etc.).

Other aspects of the disclosed subject matter, as well as features and advantages of various aspects of the disclosed subject matter, should become apparent to those of ordinary skill in the art through consideration of the ensuing description, the accompanying drawings, and the appended claims.

BRIEF DESCRIPTION OF THE DRAWINGS

In the drawings:

FIG. 8 is a cross-sectional representation of the embodiment of fragrance dispenser shown in FIG. 1;

FIG. 9 is a perspective view of an embodiment of a reservoir, or bottle, that may be used with various embodiments of fragrance dispensers, including the embodiment of fragrance dispenser shown in FIG. 1;

FIG. 10 is a side view of the embodiment of reservoir the embodiment of reservoir shown in FIG. 9;

DETAILED DESCRIPTION

FIGS. 1-8 depict an embodiment of a fragrance dispenser 10. The fragrance dispenser 10 includes a housing 20. The housing 20 defines various features and/or carries various elements of the fragrance dispenser 10. In the specific embodiment depicted by FIG. 1, the housing 20 includes a body 25 and a wall mount 30 that extends from the body 25.

Figure 4:
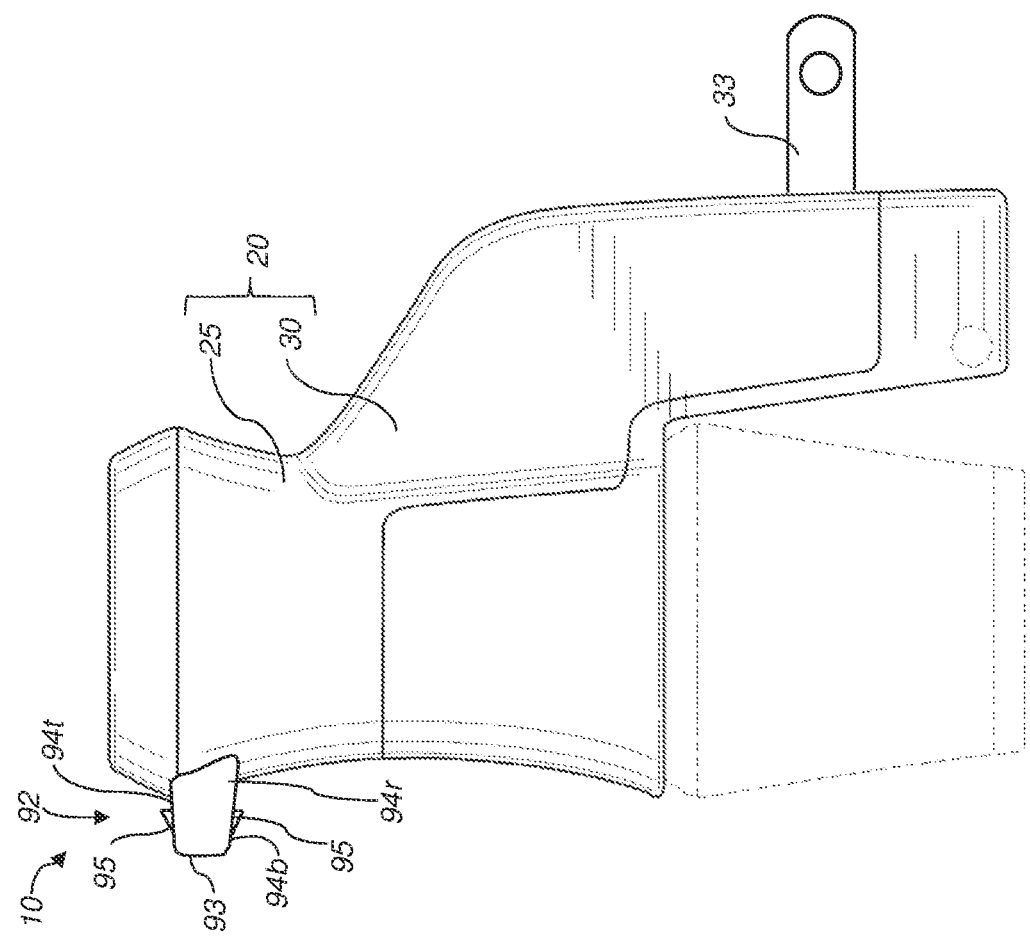
FIG. 4 is a right side view of the embodiment of fragrance dispenser shown in FIG. 1.
Figure 3:
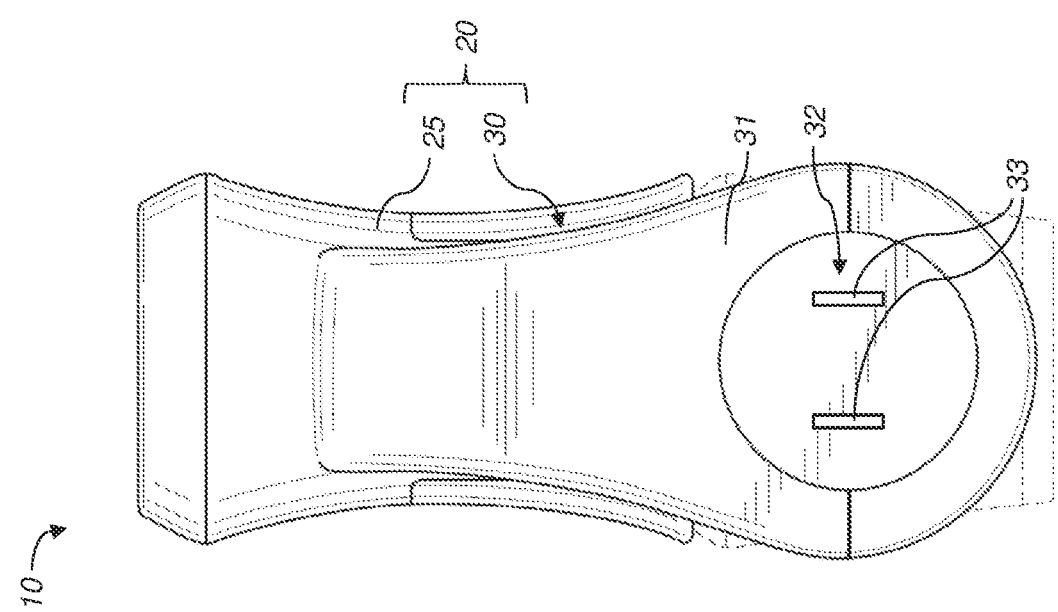
FIG. 3 is a rear view of the embodiment of fragrance dispenser shown in FIG. 1.
Figure 5:
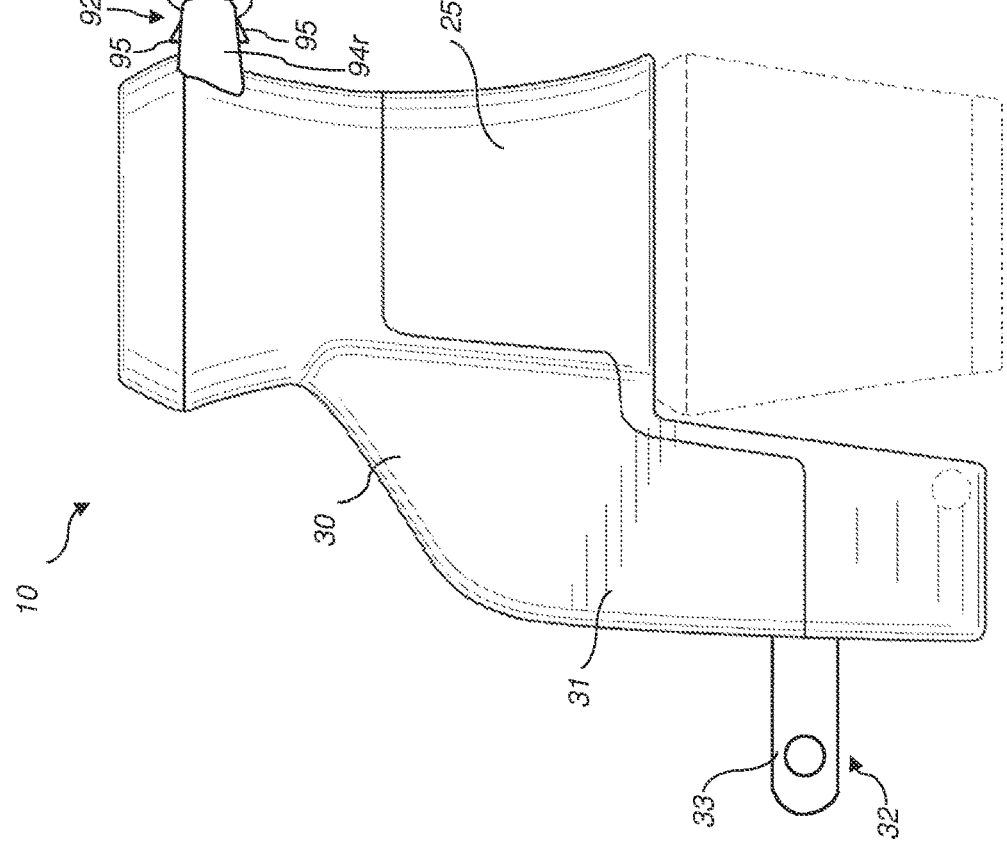
FIG. 5 is a left side view of the embodiment of fragrance dispenser shown in FIG. 1.

As illustrated by FIGS. 3-5, the wall mount 30 of the housing 20 of the fragrance dispenser 10 may include a power delivery element, such as an electrical power plug 32 that may protrude from a back side 31 of the wall mount 30. The electrical power plug 32 may be capable of coupling the fragrance dispenser 10 to an electrical outlet and of supporting the fragrance dispenser 10 once it has been coupled to the electrical outlet. The electrical power plug 32 may have a configuration that enables it to be rotated to a plurality of orientations relative to the back side 31 of the wall mount 30 (e.g., at least two perpendicular orientations, such as a first orientation in which prongs 33 of the electrical power plug 32 are oriented laterally adjacent to one another and a second orientation in which the prongs 33 are oriented vertically adjacent to one another; etc.). A rotatable electrical power plug 32 may enable the fragrance dispenser 10 to be vertically oriented regardless of the orientation of an electrical outlet with which the fragrance dispenser 10 is used.

The electrical power plug 32 may communicate electricity through the electrical outlet to electrical components carried by the wall mount 30 of the housing 20 of the fragrance dispenser 10. Without limitation, and with reference to FIG. 8, the electrical power plug 32 may supply electricity to electronics of the fragrance dispenser 10, such as a rectifier 34 (which converts alternating current (AC) to direct current (DC)), a fragrance dispersal component 35 (e.g., a fan, a heating element, a combination thereof, etc.), and/or to any other electronics of the fragrance dispenser 10. When powered on, the fragrance dispersal component 35 may facilitate the flow of air into, through, and out of the body 25 of the housing 20 of the fragrance dispenser 10.

The body 25 of the housing 20 of the fragrance dispenser 10 defines a reservoir receptacle 40 and a fragrance emission vent 50. More specifically, the reservoir receptacle 40 may be defined within a lower portion 26, or a bottom, of the body 25, while the fragrance emission vent 50 may be defined by an upper portion 28, or a top, of the body 25.

Figure 6:
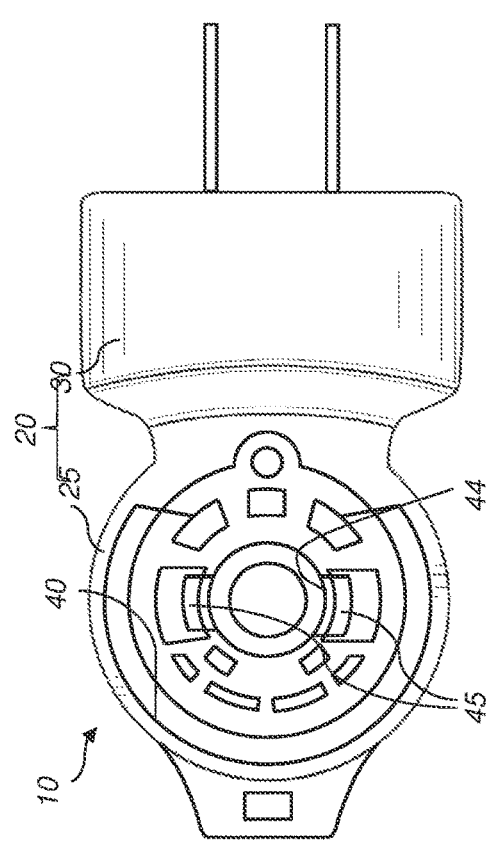
FIG. 6 is a bottom view of the embodiment of fragrance dispenser shown in FIG. 1.

With reference to FIGS. 6 and 8, as well as to FIGS. 9 and 10, the reservoir receptacle 40 has a configuration that enables it to receive an upper portion, such as a neck 72 of a reservoir 60 (e.g., a bottle, such as that depicted by FIGS. 9 and 10; a cartridge; etc.) that contains a fragrance and to orient the reservoir 60 in such a way that fragrance will be exposed to airflow generated by the fragrance dispersal component 35. The reservoir receptacle 40 may include engagement features 45 (e.g., a helical thread, one or more circumferential threads, clips, etc.) that can engage complementary engagement features 75 (e.g., a helical thread, one or more circumferential threads, a lip, recesses, etc.) of the reservoir 60. In some embodiments, the engagement features 45 may have a configuration that enables them to releasably engage the complementary engagement features 75 of the reservoir 60.

The reservoir receptacle 40 may communicate with a wick receptacle 44. As depicted, the wick receptacle 44 may be located above the reservoir receptacle 40 and comprise an extension of the reservoir receptacle 40. Thus, the wick receptacle 44 may receive an upper portion 82 of a wick 80 that protrudes from a reservoir 60 upon introduction of an upper portion (e.g., a neck 72, etc.) of the reservoir 60 into the reservoir receptacle 40 and coupling of the upper portion of the reservoir 60 to the reservoir receptacle 40 (e.g., by way of engagement features 45 of the reservoir receptacle 40 and complementary engagement features 75 of the upper portion of the reservoir 60, etc.).

The wick receptacle 44 may have a configuration that enables air flow generated by the fragrance dispersal component 35 (FIG. 8) to travel past the upper portion 82 of the wick 80 that has been disposed within the wick receptacle 44 in a manner that facilitates vaporization of fragrance that wets the wick 80. Air that flows past or through the wick receptacle 44 may then flow to and through the fragrance emission vent 50.

Figure 1:
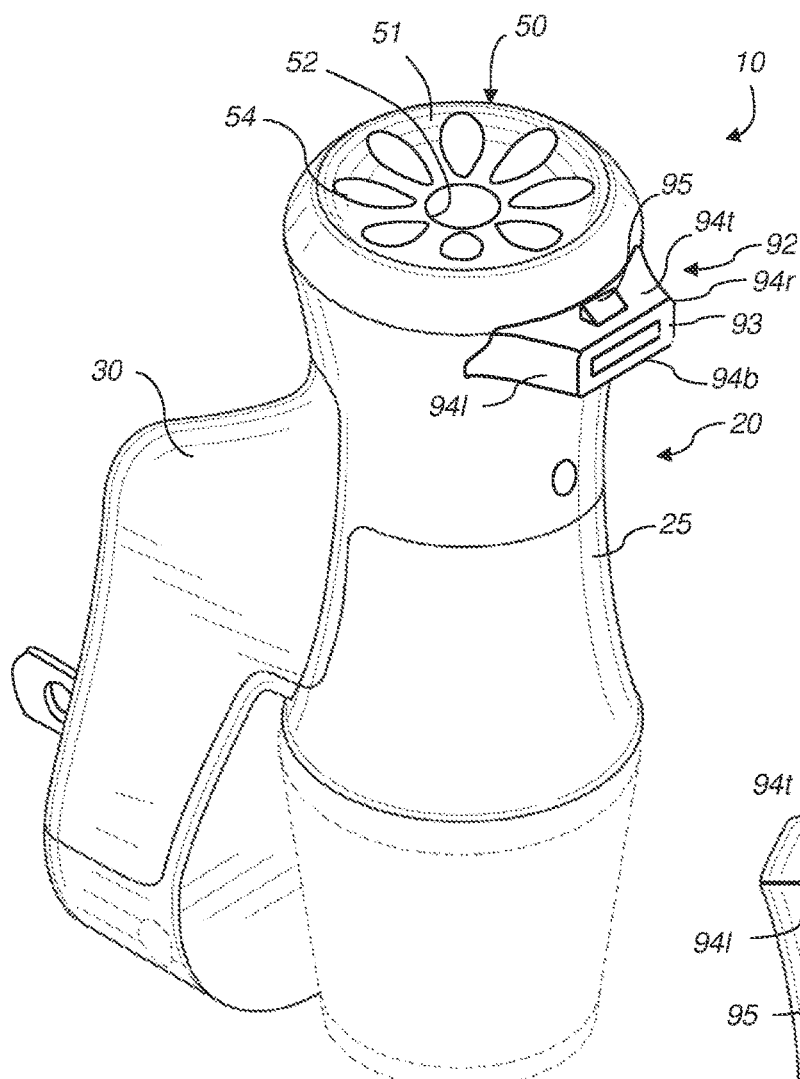
FIG. 1 is a perspective view of an embodiment of a fragrance dispenser according to this disclosure.
Figure 2:
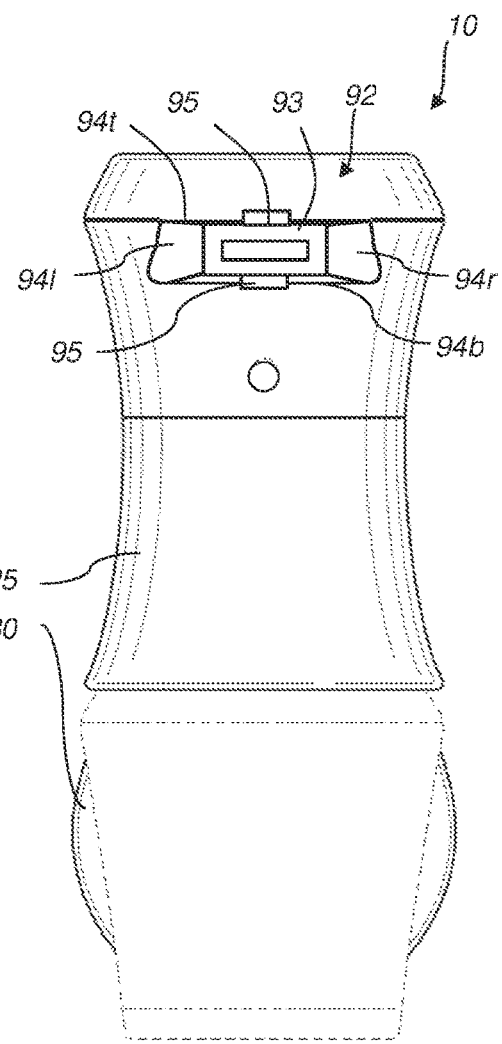
FIG. 2 is a front view of the embodiment of fragrance dispenser shown in FIG. 1.
Figure 7:
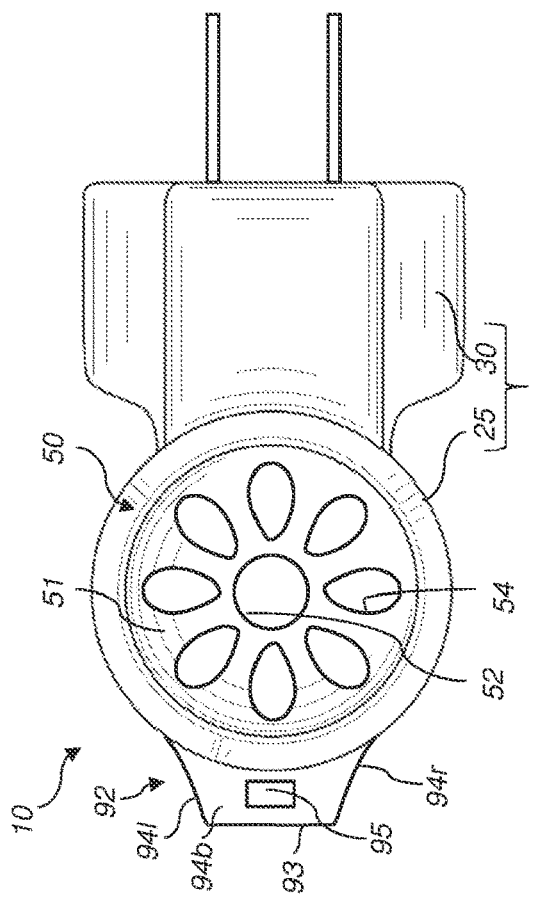
FIG. 7 is a top view of the embodiment of fragrance dispenser shown in FIG. 1.

The fragrance emission vent 50 defines a top of the body 25 of the housing 20 of the fragrance dispenser 10. A plurality of apertures 52, 54 in the fragrance emission vent 50 may enable the air flow through the body 25 to carry vaporized fragrance or, in other embodiments, atomized fragrance out of the body 25. As depicted by FIGS. 1 and 7, in a specific, but nonlimiting embodiment, the fragrance emission vent 50 may include a central aperture 52 and a plurality of radial apertures 54 positioned around the central aperture 52. The central aperture 52 may be circular in shape, while each radial aperture 54 may have a shape that resembles a blade of a fan, such as a teardrop shape, the shape of a Reuleaux triangle, or the like. Points of the radial apertures 54 may be oriented toward a center of a circle defined by the radial apertures 54, toward a center of the central aperture 52, and/or toward a center of the fragrance emission vent 50.

An outer surface 51 of the fragrance emission vent 50 may define a depression in a top of the body 25 of the housing 20 of the fragrance dispenser 10. More specifically, but without limiting this disclosure, the outer surface 51 of the fragrance emission vent 50 may define a concave depression in the top of the body 25.

A configuration of the fragrance emission vent 50 (e.g., the outer surface 51 of the fragrance emission vent 50, alone or in combination with shapes and/or arrangements of apertures 52, 54 of the fragrance emission vent 50) may generate one or more vortices as air and fragrance flow there through and/or are emitted thereby. The generation of a vortex or a plurality of vortices may optimize or otherwise tailor the direction and/or distance that fragrance may be thrown from the fragrance emission vent 50 and, thus, from the fragrance dispenser 10. The vortex or vortices may transport a fragrance captured in the airflow a greater distance than the airflow generated by the fragrance dispersal component 35 would on its own. In some embodiments, the fragrance emission vent 50 may have a configuration that generates a plurality vortices that combine to form a larger vortex.

The shape of the outer surface 51 of the fragrance emission vent 50 may enable it to collect any fragrance that flows through the apertures 52, 54, but that is not dispersed upon exiting the fragrance emission vent 50 (e.g., fragrance that has not vaporized, fragrance the condenses upon exiting the fragrance emission vent 50, etc.). With returned reference to FIG. 8, and to FIGS. 9 and 10, as fragrance collects on the outer surface 51 of the fragrance emission vent 50, the fragrance may flow through the apertures 52, 54 and be directed (e.g., funneled, etc.) toward the wick 80 and/or the opening 70 of the reservoir 60 that has been coupled to the body 25 of the housing 20 of the fragrance dispenser 10.

Figure 11:
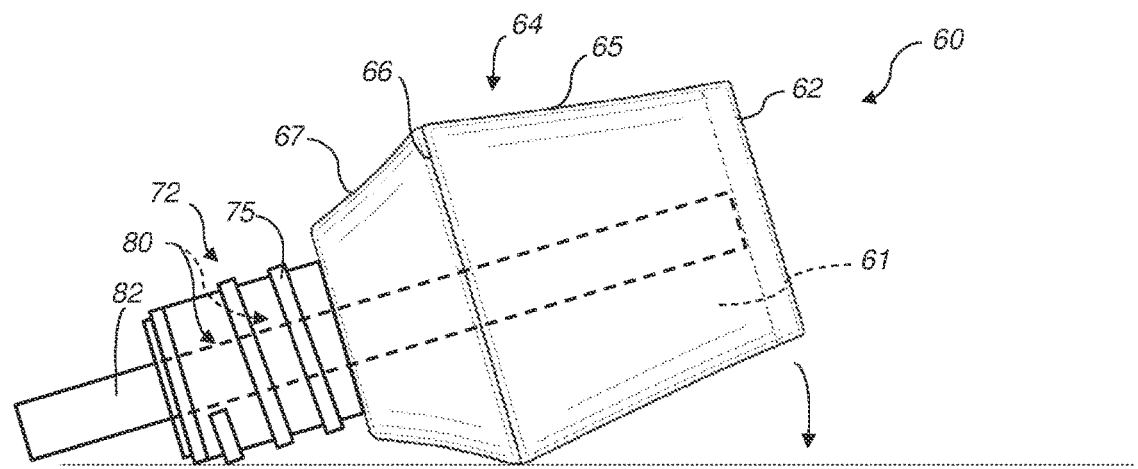
FIG. 11 shows the embodiment of reservoir depicted by FIG. 9 on its side.
Figure 12:
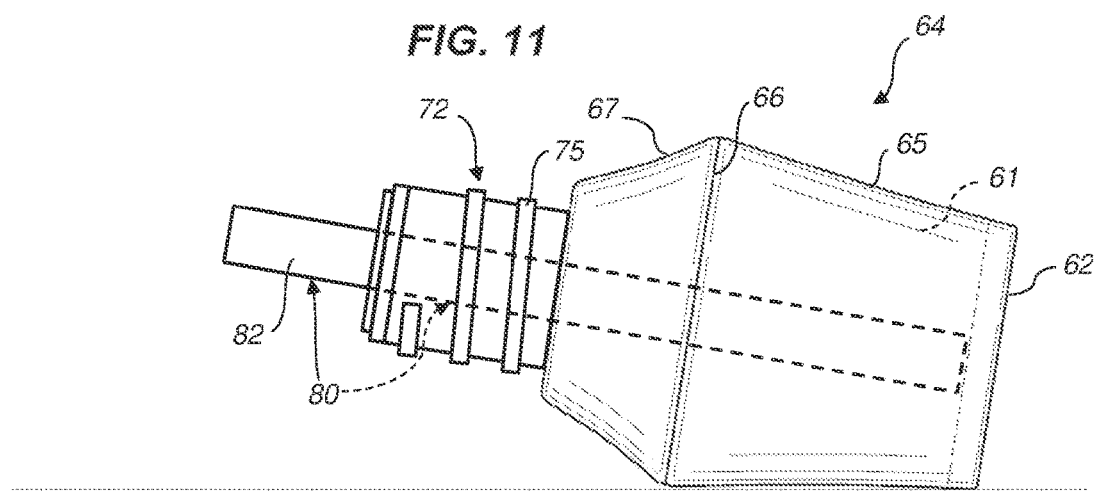
FIG. 12 illustrates a position in which the embodiment of reservoir depicted by FIG. 9 tends to orient itself when a surface of the reservoir other than its base is placed on a horizontal surface.

Referring again to FIGS. 9 and 10, an embodiment of a reservoir 60 that may be used with a variety of embodiments of fragrance dispensers, including, without limitation the embodiment of fragrance dispenser 10 depicted by and described in reference to FIGS. 1-8. A configuration of the reservoir 60 may prevent the contents thereof (e.g., a fragrance, etc.) from spilling out when the reservoir 60 rests on its side (e.g. when the reservoir 60 is knocked over onto a horizontal surface, etc.), as illustrated by FIGS. 11 and 12. More specifically, a shape of the reservoir 60 may ensure that an opening 70 of the reservoir 60 is oriented in a somewhat upward direction as the reservoir 60 rests on its side, as shown in FIG. 12.

Such a reservoir 60 may comprise a bottle with a base 62 and at least one sidewall 64 extending from the base 62. The at least one sidewall 64 may include a lower portion 65 and an upper portion 67, with a ridge 66 defining a boundary between the lower portion 65 and the upper portion 67. An interior surface of the lower portion 65 may be oriented at an obtuse angle to an interior surface of the base 62. As an example, an interior surface of the lower portion 65 may be oriented at an angle of about 100°, at an angle of about 100° to about 135°, etc., to the interior surface of the base 62, or exterior surfaces of the base 62 and the lower portion 65 may be oriented at an angle of about 260°, at an angle of about 225° to about 260°, etc., respectively, to one another. An interior surface of the upper portion 67 may be oriented at an obtuse angle to the interior surface of the lower portion 65. As an example, the interior surface of the upper portion 67 may be oriented at an angle of about 145°, at an angle of about 130° to about 160°, etc., to the interior surface of the lower portion 65, or exterior surfaces of the lower portion 65 and the upper portion 67 may be oriented at an angle of about 215°, at an angle of about 200° to about 230°, etc., respectively, to each other.

Relative dimensions (e.g., slant heights, etc.) and orientations of the lower portion 65 and the upper portion 67 may distribute a weight of the reservoir 60 in such a way that when the reservoir 60 is placed on a horizontal surface but does not rest on its base 62 (e.g., when the reservoir 60 is knocked onto its side, etc.), it tends to rest on the lower portion 65 of its sidewall 64, as shown in FIG. 12; for example, it may tip from the upper portion 67 of its sidewall 64 onto the lower portion 65 of its sidewall 64, as shown in FIGS. 11 and 12, respectively. As an example, the slant height of the lower portion 65 may be at least twice the slant height of the upper portion 67. In a specific embodiment, the base 62 may have a diameter of about 30 mm, the ridge 66 of the sidewall 64 may have a diameter of about 38 mm, the slant height of the lower portion 65 of the sidewall 64 may be about 33 mm, and the slant height of the upper portion 67 of the sidewall 64 may be about 14 mm. The exterior surface of the lower portion 65 may be oriented at an angle of about 260° to the exterior surface of the base 62 and the exterior surface of the upper portion 67 may be oriented at an angle of about 215° to the exterior surface of the lower portion 65.

An opening 70 at or adjacent to an upper extent of the sidewall(s) 64 of the reservoir 60 may provide access to the interior 61 of the reservoir 60. Optionally, the opening 70 may be defined by and extend through a neck 72 that extends from an upper extent of the sidewall(s) 64. A configuration of the neck 72 (e.g., its weight, its length, etc.) may facilitate tipping of a reservoir 60 that rests on its sidewall 64 onto the lower portion 65 of the sidewall 64 and, thus, may prevent the reservoir 60 from resting on the upper portion 67 of its sidewall 64.

A wick 80 may extend through the opening 70 and the neck 72 into the interior 61 of the reservoir 60. An upper portion 82 of the wick 80 may remain outside of the reservoir 60 and, thus, may extend beyond the upper extent of the neck 72. The extent to which the upper portion 82 of the wick 80 extends beyond the upper extent of the neck 72 may contribute to the tendency of the reservoir 60 to rest on the lower portion 65 of its sidewall 64 rather than on the upper portion 67 of its sidewall 64 and, thus, to tipping of the reservoir 60 to a position in which it rests on the lower portion 65 of its sidewall 64.

In addition to positioning the reservoir 60 in such a way that its opening 70 tends to be oriented in a somewhat upward direction, the shape and relative dimensions of the features of the reservoir 60 may enable it to retain all of its contents—i.e., prevent its contents from spilling out of the opening 70 or seeping out of the wick 80—when the reservoir 60 rests on its sidewall 64.

In addition to the above-described features, the reservoir 60 may include one or more complementary engagement features 75 (e.g., a helical thread, one or more circumferential grooves, a lip, one or more recesses, etc.). More specifically, the complementary engagement feature(s) 75 may be defined by an exterior surface of the neck 72 of the reservoir 60. The complementary engagement features 75 of the reservoir 60 may enable its coupling to a fragrance dispenser; for example, to the reservoir receptacle 40 of the embodiment of fragrance dispenser 10 shown in FIGS. 1-8.

Turning now to FIGS. 1, 2, 4, 5, and 7, a first member 92 of a charm connector 90 may be located on a front side 29 of the body 25 of the housing 20. In the embodiment depicted by FIGS. 1, 2, 4, 5, and 7, the first member 92 (e.g., a male member) of the charm connector 90 may protrude from the front side 29.

Figure 14:
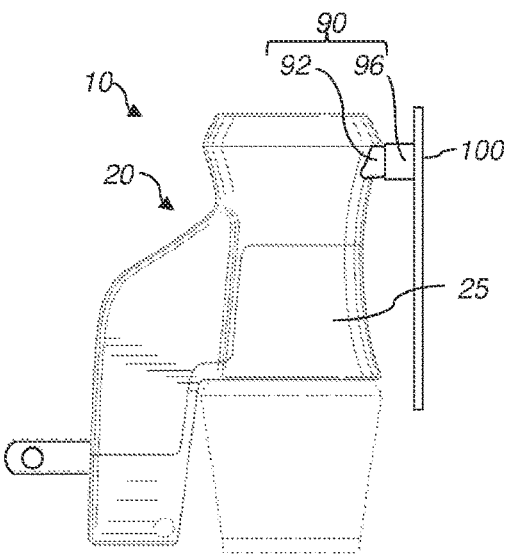
FIG. 14 illustrates use of the charm connector to secure an embodiment of a charm over the front side of the body of the housing of the fragrance dispenser.

The first member 92 of the charm connector 90 may have a configuration that facilitates assembly of a second member 96 (e.g., a female member) of the charm connector 90 thereto. FIG. 14 depicts, and U.S. Design Pat. D835,771, issued on Dec. 11, 2018 and titled CHARM CONNECTOR FOR A FRAGRANCE DISPENSER, the entire disclosure of which is hereby incorporated herein, discloses an embodiment of second member 96 that complements the embodiment of first member 92 shown in FIGS. 1, 2, 4, 5, and 7. As an example, side surfaces 94*l* and 94*r* of the first member 92 may taper outwardly from a front 93 of the first member 92 toward the front surface 29 of the body 25 of the housing 20 of the fragrance dispenser 10. Such a configuration may facilitate introduction of the first member 92 into a recess 97 of the second member 96.

Additionally, a configuration of the first member 92 of the charm connector 90 may enable the first member 92 to be secured coupled to, or mated with, the second member 96 of the charm connector 90. For example, a tapered engagement tab 95 may protrude from an exterior surface of the first member 92, such as one or both of a top surface 94*t* and a bottom surface 94*b* of the first member 92. Each tapered engagement tab 95 may be received by and, thus, engage, a corresponding recess 99 formed in or aperture that opens to corresponding top and/or bottom interior surfaces 98*t* and 98*b*, respectively, of the recess 97 of the second member 96. In some embodiments, the second member 96 may releasably couple to the first member 92 and, thus, may be uncoupled and removed from the first member 92.

Figure 13:
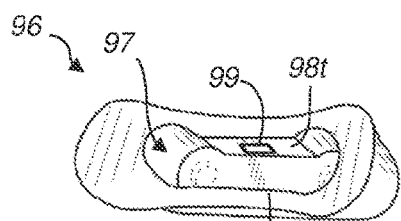
FIG. 13 provides a perspective view of an embodiment of a second member of a charm connector that may be assembled with the embodiment of the first member of the charm connector that protrudes from a front side of a body of a housing of the fragrance dispenser, as shown in FIG. 1.

The male member 92 of the charm connector 90 may enable a decorative charm 100, such as that depicted by FIG. 14, to which the female member 96 of the charm connector 90 is secured to be fasted in place over the body 25 of the housing 20 in the manner depicted by FIG. 13. In embodiments where the second member 96 may be uncoupled and removed from the first member 92, the charm connector 90 may facilitate the placement of any of a variety of different charms over the front side 29 of the body 25 of the housing 20 of the fragrance dispenser 10.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A fragrance dispenser, comprising:
   a reservoir of fragrance;
   a dispersal element capable of dispersing the fragrance to an environment in which the fragrance dispenser is located;
   a power delivery element electrically coupled to the dispersal element;
   a housing carrying the reservoir, the dispersal element, and at least a portion of the power delivery element, a top of the housing including a fragrance emission vent recessed therein, through which the fragrance is communicated from the dispersal element to the environment in which the fragrance dispenser is located, the fragrance emission vent having a configuration that:
   generates a vortex from the fragrance as the fragrance exits the housing; and/or
   collects condensed fragrance and returns the condensed fragrance to the dispersal element and/or to the reservoir.

2. The fragrance dispenser of claim 1, wherein the housing includes a reservoir coupling element for removably receiving the reservoir.

3. The fragrance dispenser of claim 1, wherein the dispersal element comprises a fan.

4. The fragrance dispenser of claim 1, wherein the power delivery element comprises a plurality of prongs capable of coupling with an electrical outlet.

5. The fragrance dispenser of claim 1, comprising a concave depression in the top of the housing.

6. The fragrance dispenser of claim 5, wherein openings of the fragrance emission vent have teardrop shapes.

7. The fragrance dispenser of claim 6, wherein the openings are arranged in a circle, with points of the openings oriented toward a center of the circle.

8. The fragrance dispenser of claim 1, further comprising:
   a charm connector on a front of the housing, the charm connector capable of coupling a decorative charm to the housing.

9. The fragrance dispenser of claim 8, wherein the charm connector is capable of releasably coupling any of a plurality of decorative charms to the housing.

10. A fragrance dispenser, comprising:
    a reservoir of fragrance, the reservoir having a configuration that prevents spilling of the fragrance therefrom, the reservoir including:
    a base;
    at least one sidewall extending from the base, the at least one sidewall including a lower portion and an upper portion, a ridge defined at a boundary between the lower portion and the upper portion, orientations and slant heights of the lower portion and the upper portion imparting the reservoir with a tendency, when resting on the at least one sidewall, to tilt onto the lower portion; and
    an opening at or adjacent to an upper extent of the upper portion of the at least one sidewall;
    a dispersal element capable of dispersing the fragrance to an environment in which the fragrance dispenser is located;
    a power delivery element electrically coupled to the dispersal element;
    a housing carrying the reservoir, the dispersal element, and at least a portion of the power delivery element, the housing including a fragrance emission vent through which the fragrance is communicated from the dispersal element to the environment in which the fragrance dispenser is located.

11. The fragrance dispenser of claim 10, wherein the fragrance emission vent has a configuration that:
    generates a vortex from the fragrance as the fragrance exits the housing; and/or
    collects condensed fragrance and returns the condensed fragrance to the dispersal element and/or to the reservoir.

12. A reservoir for use with a fragrance dispenser, comprising:
    a base;
    at least one sidewall extending from the base, the at least one sidewall including a lower portion and an upper portion, a ridge defined at a boundary between the lower portion and the upper portion, a slant height of the lower portion being at least double a slant height of the upper portion, orientations and slant heights of the lower portion and the upper portion imparting the reservoir with a tendency, when resting on the at least one sidewall, to tilt onto the lower portion; and
    an opening at or adjacent to an upper extent of the upper portion of the at least one sidewall.

13. The reservoir of claim 12, wherein:
    exterior surfaces of the base and the lower portion of the at least one sidewall are oriented at an angle of about 225° to about 260° to one another; and
    exterior surfaces of the lower portion of the at least one sidewall and the upper portion of the at least one sidewall are oriented at an angle of about 200° to about 230° to one another.

14. The reservoir of claim 12, further comprising:
    a neck defining the opening, extending from an upper extent of the upper portion of the at least one sidewall, and having a length that contributes to the tendency of the reservoir, when resting on the at least one sidewall, to tilt onto the lower portion of the at least one sidewall.

15. The reservoir of claim 14, further comprising:
    a wick extending through the neck, with an upper portion of the wick protruding beyond an upper extent of the neck, the upper portion of the wick contributing to the tendency of the reservoir, when resting on the at least one sidewall, to tilt onto the lower portion of the at least one sidewall.

16. The reservoir of claim 14, further comprising:
at least one engagement element on the neck, the at least one engagement element capable of being engaged by a complementary engagement element of a fragrance dispenser.

17. A fragrance dispenser, comprising:
a reservoir of fragrance;
a dispersal element capable of dispersing the fragrance to an environment in which the fragrance dispenser is located;
a power delivery element electrically coupled to the dispersal element;
a housing carrying the reservoir, the dispersal element, and at least a portion of the power delivery element, the housing including a fragrance emission vent through which the fragrance is communicated from the dispersal element to the environment in which the fragrance dispenser is located, the fragrance emission vent having a configuration that:
  generates a vortex from the fragrance as the fragrance exits the housing; and/or
  collects condensed fragrance and returns the condensed fragrance to the dispersal element and/or to the reservoir; and
a charm connector on a front of the housing, the charm connector capable of coupling a decorative charm to the housing.

18. The fragrance dispenser of claim 17, wherein the charm connector is capable of releasably coupling any of a plurality of decorative charms to the housing.

19. A reservoir for use with a fragrance dispenser, comprising:
a base;
at least one sidewall extending from the base, the at least one sidewall including a lower portion and an upper portion, a ridge defined at a boundary between the lower portion and the upper portion, orientations and slant heights of the lower portion and the upper portion imparting the reservoir with a tendency, when resting on the at least one sidewall, to tilt onto the lower portion;
a neck extending from an upper extent of the upper portion of the at least one sidewall and having a length that contributes to the tendency of the reservoir, when resting on the at least one sidewall, to tilt onto the lower portion of the at least one sidewall; and
an opening defined by the neck.

20. The reservoir of claim 19, further comprising:
a wick extending through the neck, with an upper portion of the wick protruding beyond an upper extent of the neck, the upper portion of the wick contributing to the tendency of the reservoir, when resting on the at least one sidewall, to tilt onto the lower portion of the at least one sidewall.

21. The reservoir of claim 19, further comprising:
at least one engagement element on the neck, the at least one engagement element capable of being engaged by a complementary engagement element of a fragrance dispenser.

* * * * *